(12) United States Patent
Norton

(10) Patent No.: US 10,499,902 B2
(45) Date of Patent: Dec. 10, 2019

(54) REPAIR DEVICE AND METHOD FOR DEPLOYING ANCHORS

(71) Applicant: Biomet Sports Medicine, LLC, Warsaw, IN (US)

(72) Inventor: Daniel R. Norton, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 236 days.

(21) Appl. No.: 15/482,106

(22) Filed: Apr. 7, 2017

(65) Prior Publication Data
US 2017/0290579 A1 Oct. 12, 2017

Related U.S. Application Data

(60) Provisional application No. 62/320,860, filed on Apr. 11, 2016.

(51) Int. Cl.
*A61B 17/04* (2006.01)
*A61B 17/06* (2006.01)
(Continued)

(52) U.S. Cl.
CPC .... *A61B 17/0401* (2013.01); *A61B 17/06066* (2013.01); *A61B 17/3468* (2013.01);
(Continued)

(58) Field of Classification Search
CPC .............................................. A61B 2017/0409
See application file for complete search history.

(56) References Cited

U.S. PATENT DOCUMENTS 5,810,848 A * 9/1998 Hayhurst ............... A61B 17/04
606/139
2007/0185532 A1 8/2007 Stone et al.
(Continued)

FOREIGN PATENT DOCUMENTS

WO WO-2009124215 A1 10/2009
WO 2017180473 10/2017

OTHER PUBLICATIONS

"Australian Application Serial No. 2017249136, Response Filed Feb. 28, 2019 to First Examination Report dated Dec. 18, 2018", 25 pgs.
(Continued)

*Primary Examiner* — Todd J Scherbel
(74) *Attorney, Agent, or Firm* — Schwegman Lundberg & Woessner, P.A.

(57) ABSTRACT

A bone or tissue repair device can deploy first and second anchors from a distal end of a bore of a needle. A cylindrical first anchor can be disposed in the bore proximal to a distal end of the bore. A cylindrical second anchor can be disposed in the bore proximal to the first anchor. A pusher wire can include teeth positioned at a distal end of the pusher wire. The pusher wire and teeth can be configured to engage an interior of the first anchor; advance distally, with respect to the needle, to force the first anchor distally out of the bore; retract proximally, with respect to the needle and the second anchor, to position the teeth inside an interior of the second anchor; engage the interior of the second anchor; and advance distally, with respect to the needle, to force the second anchor distally out of the bore.

17 Claims, 20 Drawing Sheets

(51) Int. Cl.
    *A61B 90/00*     (2016.01)
    *A61B 17/34*     (2006.01)
    *A61B 17/00*     (2006.01)

(52) U.S. Cl.
    CPC .... *A61B 90/03* (2016.02); *A61B 2017/00473* (2013.01); *A61B 2017/0409* (2013.01); *A61B 2017/0464* (2013.01); *A61B 2017/06071* (2013.01); *A61B 2090/034* (2016.02); *A61B 2090/062* (2016.02); *A61B 2090/0811* (2016.02)

(56) References Cited

U.S. PATENT DOCUMENTS

| | | |
|---|---|---|
| 2008/0140093 A1 | 6/2008 | Stone et al. |
| 2011/0071549 A1 | 3/2011 | Caborn et al. |
| 2011/0306989 A1 | 12/2011 | Darois et al. |
| 2014/0114330 A1* | 4/2014 | Karasic .............. A61B 17/0401 606/144 |

OTHER PUBLICATIONS

"Australian Application Serial No. 2017249136, First Examination Report dated Dec. 18, 2018", 5 pgs.
"International Serial No. PCT/US2017/026625, International Search Report dated Jul. 13, 2017", 7 pgs.
"International Application Serial No. PCT/US2017/026625, Written Opinion dated Jul. 13, 2017", 12 pgs.
"European Application Serial No. 17718320.9, Response filed Jun. 3, 2019 to Office Action dated Nov. 21, 2018", 18 pgs.

* cited by examiner

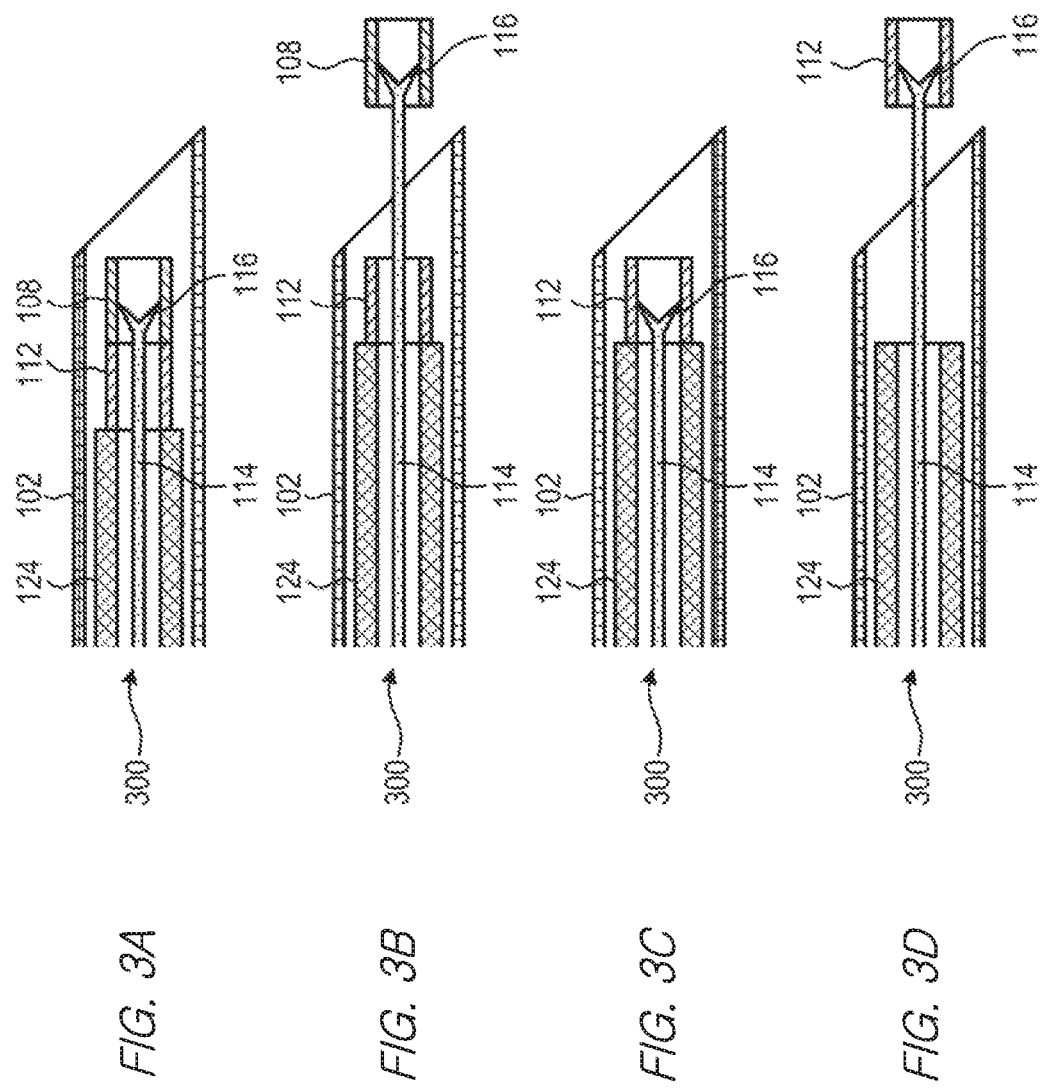

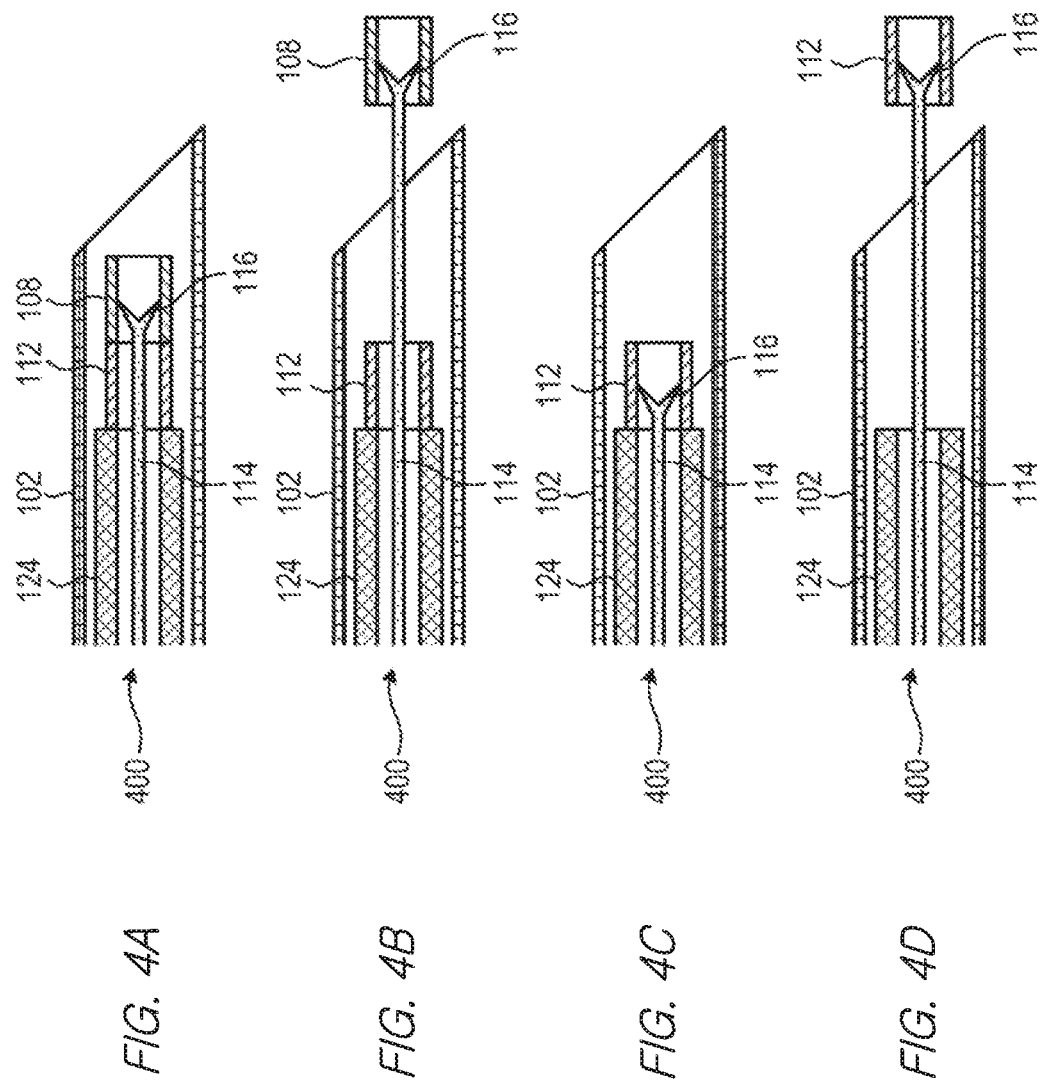

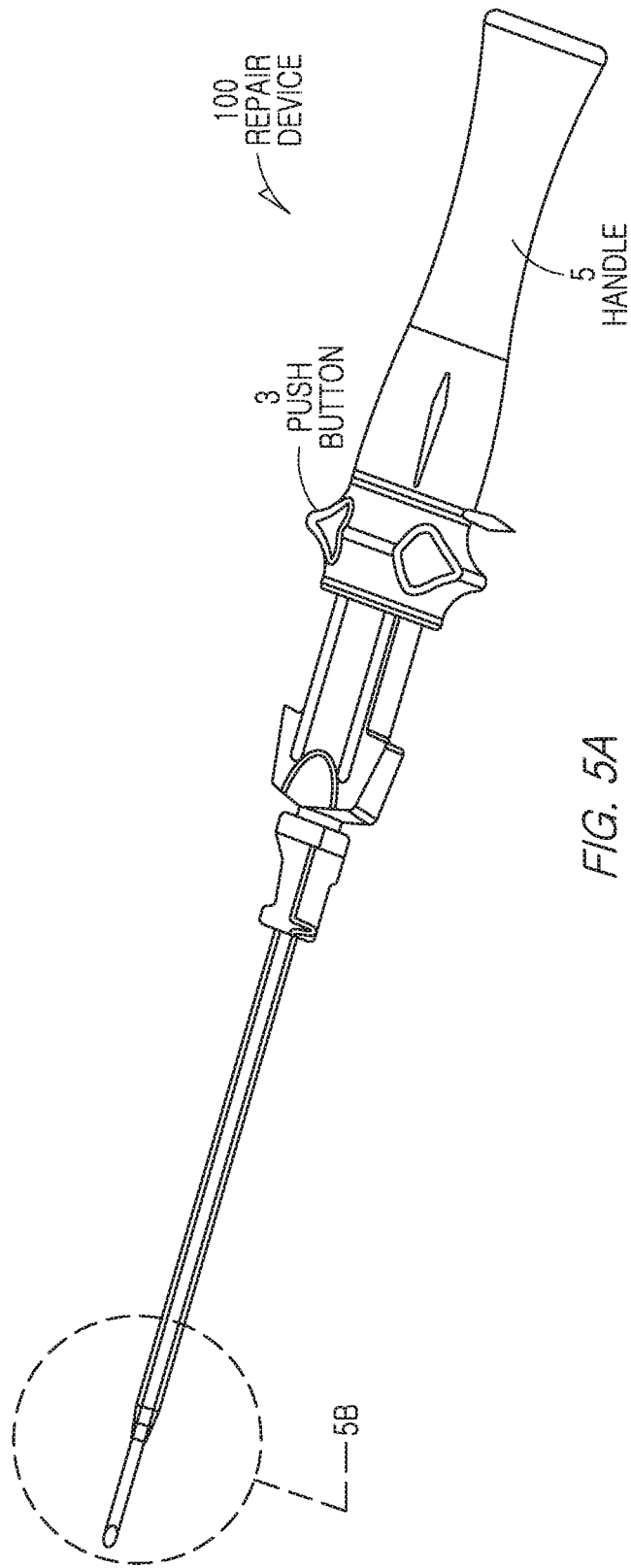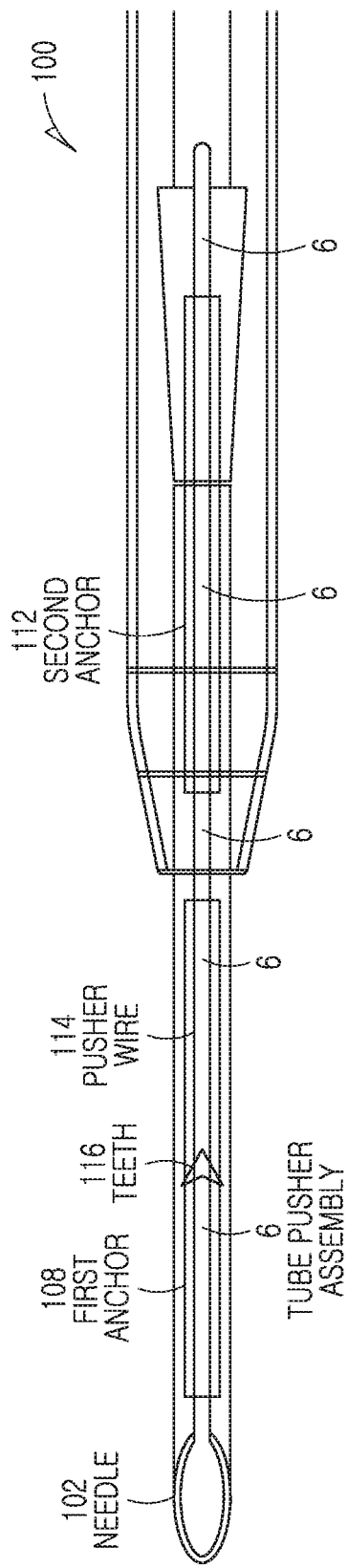
FIG. 5A
FIG. 5B

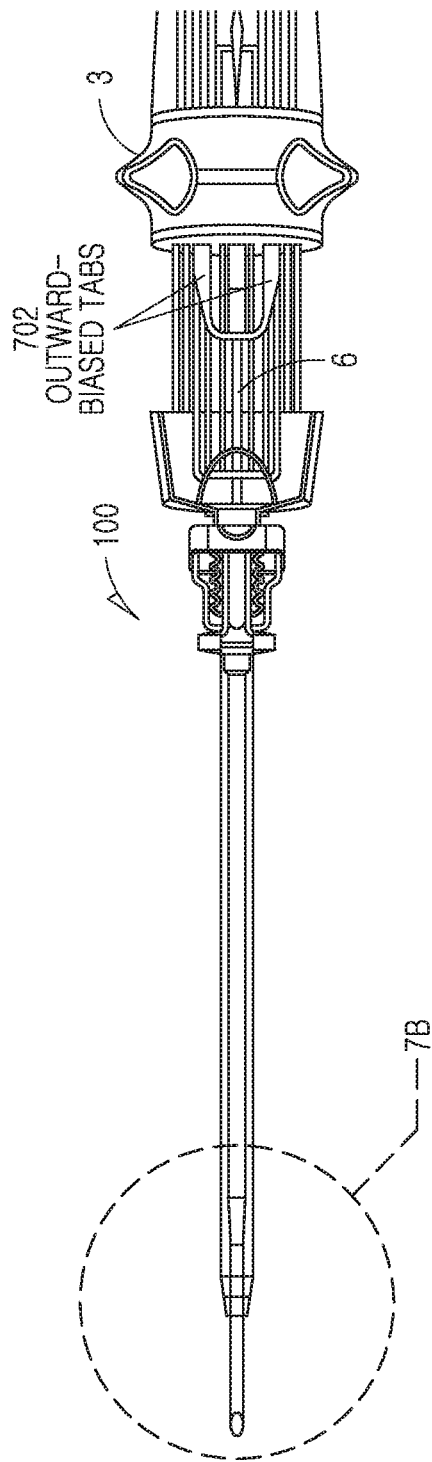
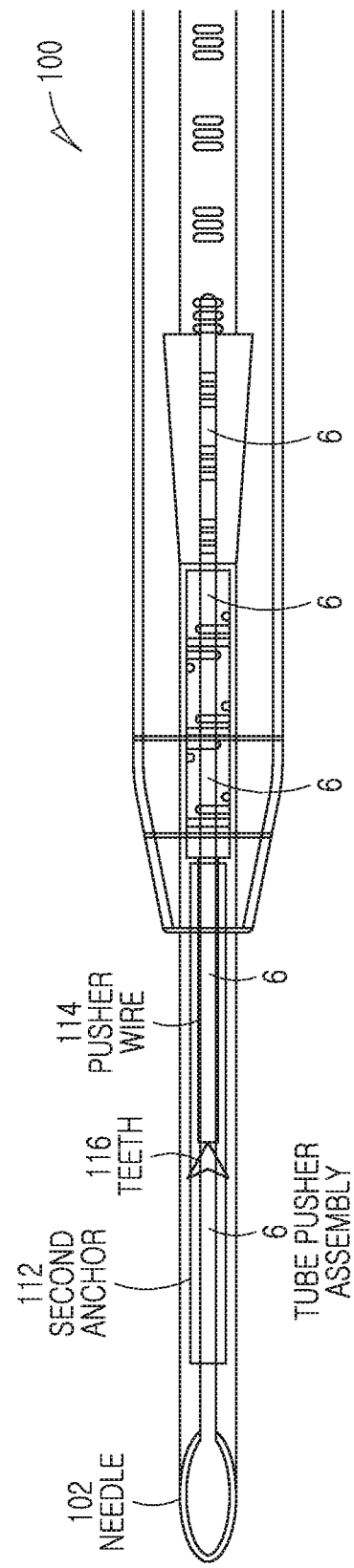
FIG. 7A
FIG. 7B

REPAIR DEVICE AND METHOD FOR DEPLOYING ANCHORS

CLAIM OF PRIORITY

This application claims the benefit of priority to U.S. Provisional Application Ser. No. 62/320,860, filed on Apr. 11, 2016, which is incorporated herein by reference in its entirety.

FIELD OF THE DISCLOSURE

The present disclosure relates to deploying anchors for bone or tissue repair surgery.

BACKGROUND OF THE DISCLOSURE

In the human body, bone or tissue can require repair. For example, a meniscus is a fibrocartilaginous structure found within a joint, such as a knee joint. Forceful twisting or rotation of the knee (or other joint) can tear the meniscus, which can require surgical repair of the meniscus.

SUMMARY

In a first embodiment, a bone or tissue repair device can deploy first and second anchors from a distal end of a bore of a needle. A cylindrical first anchor can be sized and shaped to be disposed in the bore proximal to a distal end of the bore. A cylindrical second anchor can be sized and shaped to be disposed in the bore proximal to the first anchor. A pusher wire can include teeth positioned at a distal end of the pusher wire. The teeth can be configured to engage an interior of the first anchor; advance distally, with respect to the needle, to force the first anchor distally out of the bore; retract proximally, with respect to the needle and the second anchor, to position the teeth inside an interior of the second anchor; engage the interior of the second anchor; and advance distally, with respect to the needle, to force the second anchor distally out of the bore.

In a second embodiment, a method for deploying first and second anchors from a distal end of a bore of a needle can include engaging an interior of the first anchor with teeth, the teeth being positioned at a distal end of a pusher wire. The method can further include advancing the pusher wire distally, with respect to the needle, to force the first anchor distally out of the bore. The method can further include retracting the pusher wire proximally, with respect to the needle and the second anchor, to position the teeth inside an interior of the second anchor. The method can further include engaging the interior of the second anchor with the teeth. The method can further include advancing the pusher wire distally, with respect to the needle, to force the second anchor distally out of the bore.

In a third embodiment, a bone or tissue repair device can include a needle defining a bore extending through a distal end of the needle. A cylindrical first anchor can be disposed in the bore proximal to a distal end of the bore. A cylindrical second anchor can be disposed in the bore proximal to the first anchor and connected to the cylindrical first anchor by an adjustable suture loop. A pusher wire can have an outer diameter smaller than respective inner diameters of the first and second anchors, so that the pusher wire is non-engagingly slidable through the first and second anchors in the proximal and distal directions. The pusher wire can include teeth positioned at a distal end of the pusher wire. The teeth can being sized and shaped to: catch and engage on interiors of the first and second anchors when the pusher wire and teeth are advanced distally with respect to the first and second anchors, respectively; and slide along the interiors of the first and second anchors non-damagingly when the pusher wire and teeth are retracted proximally with respect to the first and second anchors, respectively. A tube pusher can be positioned over the pusher wire within the bore of the needle. The tube pusher can have a distal portion that extends radially beyond an outer circumference of the second anchor, so that the tube pusher pushes the second anchor distally as the tube pusher advances distally within the bore of the needle. A handle can be fixedly coupled to a proximal end of the needle. A push button can be disposed on an exterior of the handle, the push button being slidable proximally and distally with respect to the handle between a first proximal position and a first distal position. The push button can be coupled to the pusher wire so that proximal and distal movement of the push button produces proximal and distal movement of the pusher wire and teeth.

BRIEF DESCRIPTION OF THE DRAWINGS

FIGS. 3A-D show cross-sectional views of a second example of a deployment scheme for a repair device, in four sequential stages of use, in accordance with some embodiments.

FIGS. 4A-D show cross-sectional views of a third example of a deployment scheme for a repair device, in four sequential stages of use, in accordance with some embodiments.

FIG. 5A shows a perspective view of an example of a repair device prior to use, in accordance with some embodiments. FIG. 5B shows a cutaway view of the distal portion of the repair device of FIG. 5A, in accordance with some embodiments.

FIG. 7A shows a perspective view of the example of the repair device of FIGS. 5-6, after the first anchor has been deployed, and after the push button has been retracted proximally to its original location, in accordance with some embodiments. FIG. 7B shows a cutaway view of the distal portion of the repair device of FIG. 7A, in accordance with some embodiments.

Corresponding reference characters indicate corresponding parts throughout the several views. Elements in the drawings are not necessarily drawn to scale. The configurations shown in the drawings are merely examples, and should not be construed as limiting the scope of the invention in any manner.

DETAILED DESCRIPTION

To repair a bone or tissue structure in the human body, such as a tear in the meniscus, a surgeon can deploy two soft anchors connected by a loop of suture. The surgeon can use a repair device to pierce the tissue on one side of the tear, deploy an anchor, pull the repair device back through the tissue, pierce the tissue on the other side of the tear, and deploy a second anchor. The surgeon can pull on the suture to draw the two deployed anchors together, which can close the tear. The surgeon can then cut the suture.

There is ongoing effort to improve the repair devices, such as making the devices smaller, easier to use, and less prone to damage surrounding tissue during a repair procedure.

Figure 1:
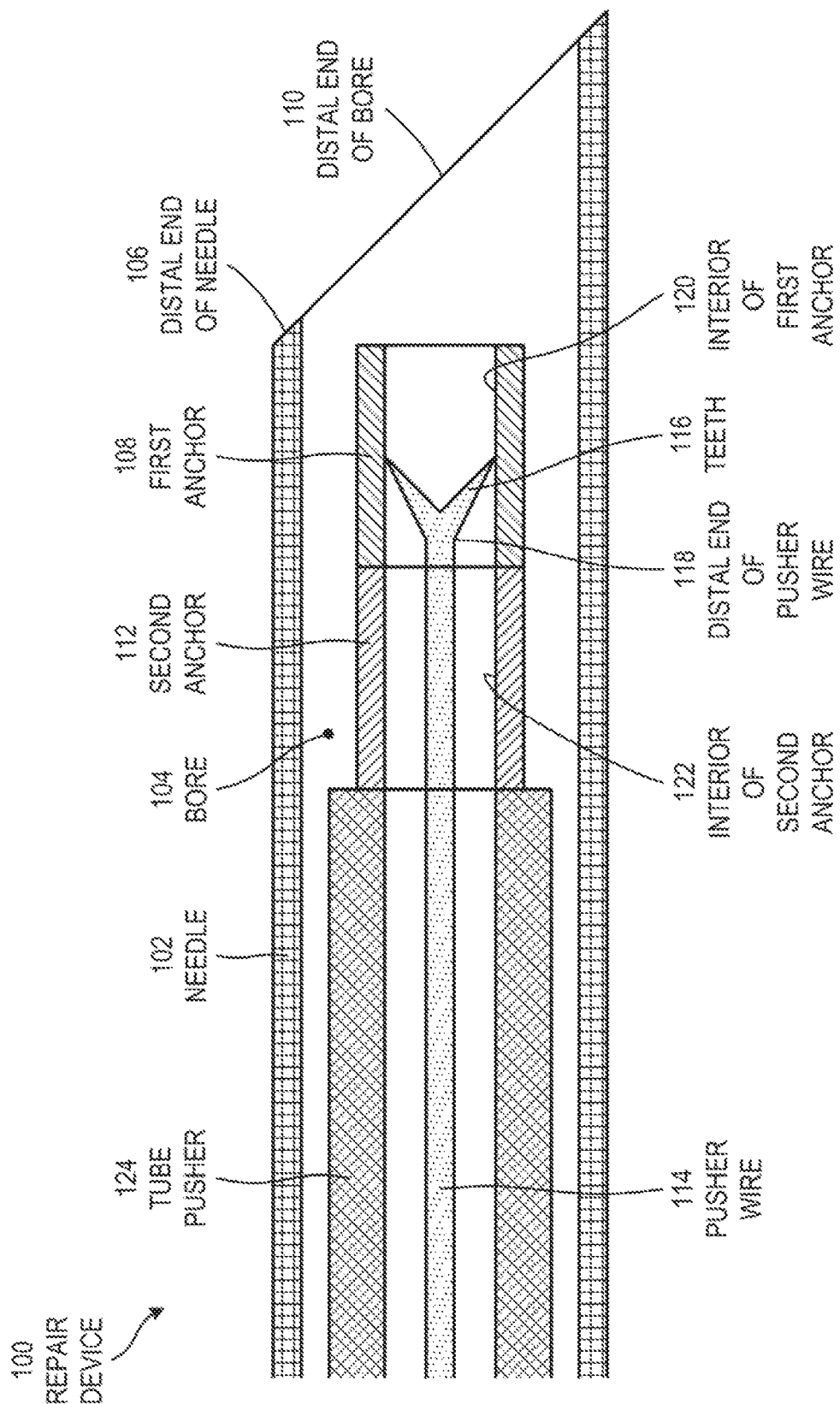
FIG. 1 shows a cross-sectional view of a distal portion of an example of a repair device prior to use, in accordance with some embodiments.

FIG. 1 shows a cross-sectional view of a distal portion of an example of a repair device 100 prior to use, in accordance with some embodiments. FIGS. 5-11, discussed below, show the full device. The configuration of FIG. 1 is but one example of a repair device 100; other configurations can also be used.

A needle 102 can define a bore 104 extending through a distal end 106 of the needle 102. In some of the specific examples presented below, the needle 102 has a curved distal portion. In other examples, the needle 102 can have a straight distal portion. In some examples, the needle 102 can have an angled distal end 106; in other examples, the needle 102 can have a straight distal end 106 (e.g., perpendicular to a longitudinal axis of the needle 102).

A cylindrical first anchor 108 can be disposed in the bore 104 proximal to a distal end 110 of the bore 104. A cylindrical second anchor 112 can be disposed in the bore 104 proximal to the first anchor 108. In some examples, the first 108 and second 112 anchors are placed into the bore during assembly of the repair device 100, so that the repair device 100 can be sold or purchased in an assembled state, prior to use. In other examples, the first 108 and second 112 anchors can be packaged separately, and can be inserted into the repair device 100 prior to use.

In some examples, the first 108 and second 112 anchors can be made from a relatively soft material, and can bend and deform under the force of a suture or other elements on the repair device 100. In some examples, the first 108 and second 112 anchors can be nominally shaped as cylinders, or tubes having a circular or elongated cross-section, but can be deformed during assembly into the repair device 100 and/or during deployment. In some examples, the term cylindrical is intended to signify that the anchor has a cross-section that is invariant from one longitudinal end of the anchor to the opposite longitudinal end of the anchor. In these examples, the anchors can have a hollow interior. In some examples, the first 108 and second 112 anchors can be connected by an adjustable suture loop (shown in FIG. 10).

A pusher wire 114 can have an outer diameter smaller than respective inner diameters of the first 108 and second 112 anchors, so that the pusher wire 114 is non-engagingly slidable through the first 108 and second 112 anchors in the proximal and distal directions. The pusher wire 114 can be capable of transmitting a pushing force in the distal direction and a pulling force in the proximal direction. The pusher wire 114 can be actuated from a proximal portion of the pusher wire 114 (shown in FIGS. 5-9 and 11).

The pusher wire 114 can include teeth 116 positioned at a distal end 118 of the pusher wire 114. In some examples, the teeth 116 can be sized and shaped to catch and engage on interiors of the first and second anchors when the pusher wire and teeth are advanced distally with respect to the first and second anchors, respectively. In some examples, the teeth 116 can be sized and shaped to slide along the interiors of the first and second anchors non-damagingly when the pusher wire and teeth are retracted proximally with respect to the first and second anchors, respectively.

The pusher wire 114 and teeth 116 can be configured to engage an interior 120 of the first anchor 108. The pusher wire 114 and teeth 116 can be further configured to advance distally, with respect to the needle 102, to force the first anchor 108 distally out of the bore 104. The pusher wire 114 and teeth 116 can be further configured to retract proximally, with respect to the needle 102 and the second anchor 112, to position the teeth 116 inside an interior 122 of the second anchor 112. The pusher wire 114 and teeth 116 can be further configured to engage the interior 122 of the second anchor 112. The pusher wire 114 and teeth 116 can be further configured to advance distally, with respect to the needle 102, to force the second anchor 112 distally out of the bore 104.

A tube pusher 124 can be positioned over the pusher wire 114 within the bore 104 of the needle 102. The tube pusher 124 can have a distal portion that extends radially beyond an outer circumference of the second anchor 112, so that the tube pusher 124 can push the second anchor 112 distally as the tube pusher 124 advances distally within the bore 104 of the needle 102. The tube pusher 124 can be actuated from a proximal portion of the tube pusher 124 (shown in FIGS. 5-9 and 11).

To actuate the pusher wire 114 and the tube pusher 124, a surgeon can slide a push button on a handle fixedly coupled to a proximal end of the needle 102. The push button can be slidable proximally and distally with respect to the handle between a first proximal position and a first distal position. The push button can be coupled to the pusher wire 114 so that proximal and distal movement of the push button produces proximal and distal movement of the pusher wire 114 and teeth 116. FIGS. 5-9 and 11 below show a detailed example of a handle, a push button, and the mechanism used to couple motion of the push button to motion of the pusher wire 114 and tube pusher 124.

FIG. 1 shows the repair device 100 in a fully assembled state, prior to use. In this assembled state, the first anchor 108 is positioned in the bore 104, the second anchor 112 is positioned in the bore 104 proximal to the first anchor 108, the pusher wire 114 extends distally through the second anchor 112 to the first anchor 108, the teeth 116 on the distal end 118 of the pusher wire 114 are positioned inside the first anchor 108, and the tube pusher 124 is positioned over the pusher wire 114 and proximal to the second anchor 112.

During use, there are several schemes for which the pusher wire 114 and teeth 116, and the tube pusher 124, can deploy the first 108 and second 112 anchors. These schemes can include different motions, different stopping points on ranges of travel, and/or different pairings of motions for the pusher wire/teeth and tube pusher. FIGS. 2-4 show three examples of deployment schemes for the repair device 100 of FIG. 1. It will be understood that these are merely examples, and that other deployment schemes can also be used. In each of these deployment schemes, a handle of the repair device 100 and its associated mechanical components can actuate the pusher wire 114 and tube pusher 124 in a manner suitable to produce the corresponding deployment scheme.

FIGS. 2A-D show cross-sectional views of a first example of a deployment scheme for a repair device 200, in four sequential stages of use, in accordance with some embodiments.

Figures 2A, 2B, 2C, 2D:
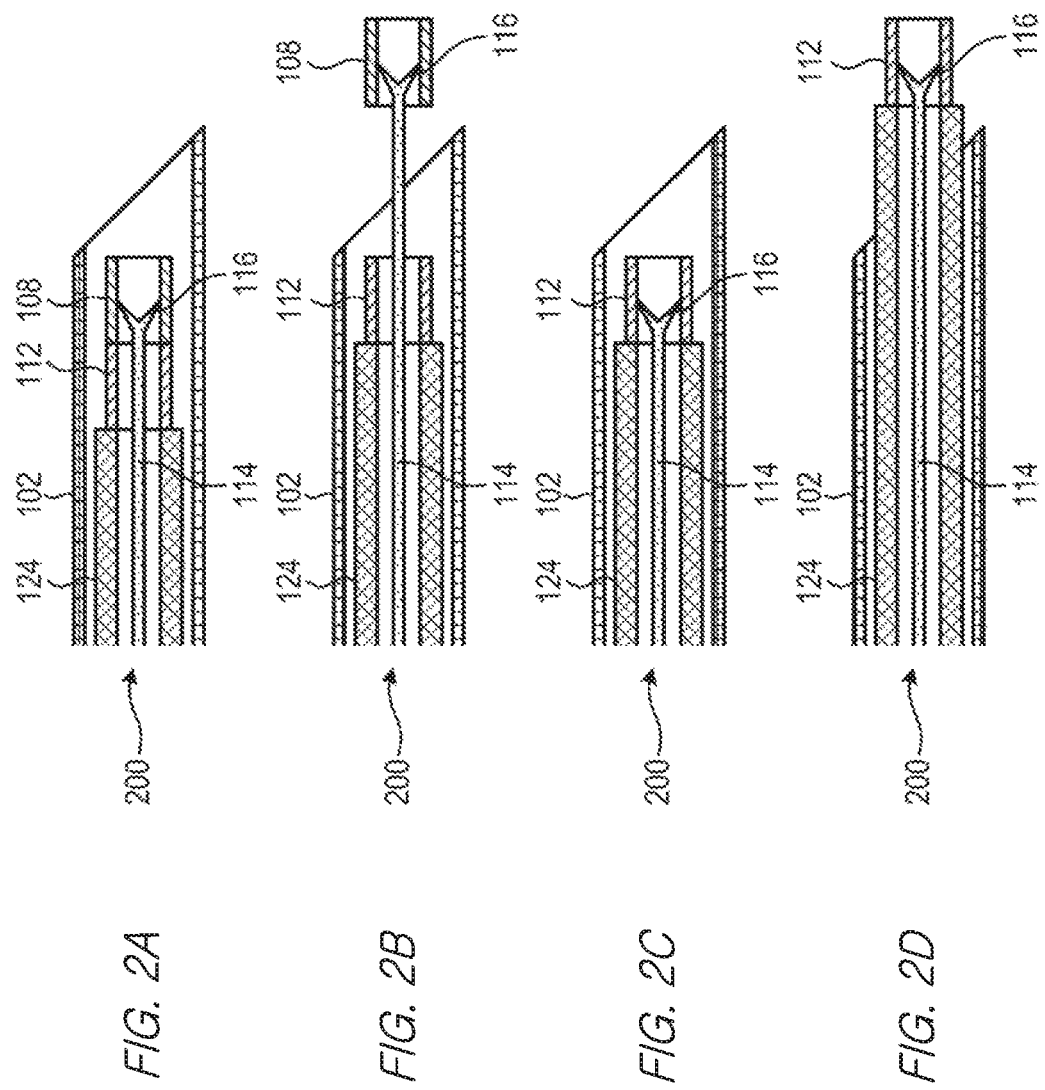
FIGS. 2A-D show cross-sectional views of a first example of a deployment scheme for a repair device, in four sequential stages of use, in accordance with some embodiments.

In FIG. 2A, the repair device 200 is shown in an assembled state, prior to use. In some examples, in the assembled state, prior to use, a push button on a handle is positioned at a first proximal position.

During use, in a first motion, a surgeon slides the push button distally to a first distal position on the handle, which can be a distal end of a range of travel for the push button. The handle can emit an audible click when the push button reaches the first distal position on the handle. FIG. 2B shows the repair device 200 after this first motion. In the deployment scheme of FIGS. 2A-D, the first motion advances the pusher wire 114 distally, to deploy the first anchor 108. In the deployment scheme of FIGS. 2A-D, the first motion also advances the tube pusher 124 distally, to distally advance the second anchor 112 to occupy approximately the same location held by the first anchor 108 prior to use (FIG. 2A).

During use, in a second motion, the surgeon slides the push button proximally, to a first proximal position on the handle, which can be a proximal end of a range of travel for the push button. The handle can emit an audible click when the push button reaches the first proximal position on the handle. FIG. 2C shows the repair device 200 after this second motion. In the deployment scheme of FIGS. 2A-D, the second motion retracts the pusher wire 114 proximally, to position the teeth 116 inside the second anchor 112. In the example of FIGS. 2A-D, the second motion positions the teeth 116 at the same position held by the teeth 116 prior to use (FIG. 2A). In the deployment scheme of FIGS. 2A-D, the second motion does not reposition the tube pusher 124 (e.g., does not move the tube pusher 124 proximally).

During use, in a third motion, the surgeon slides the push button distally back to the first distal position on the handle, which can be a distal end of a range of travel for the push button. The handle can emit another audible click when the push button again reaches the first distal position on the handle. FIG. 2D shows the repair device 200 after this third motion. In the deployment scheme of FIGS. 2A-D, the third motion advances the pusher wire 114 distally, to deploy the second anchor 112. In the deployment scheme of FIGS. 2A-D, the third motion also advances the tube pusher 124 distally, to follow the distal motion of the pusher wire 114.

FIGS. 3A-D show cross-sectional views of a second example of a deployment scheme for a repair device 300, in four sequential stages of use, in accordance with some embodiments.

The assembled state (FIG. 3A), the state after the first motion (FIG. 3B), and the state after the second motion (FIG. 3C) are the same as the corresponding states shown in FIGS. 2A-C.

The third motion differs from the deployment scheme of FIG. 2A-D, in that the third motion advances the pusher wire 114 distally, to deploy the second anchor 112, but does not advance the tube pusher 124 distally. In the state after the third motion (FIG. 3D), the tube pusher 124 remains at the same location as after the second motion (FIG. 3C).

FIGS. 4A-D show cross-sectional views of a third example of a deployment scheme for a repair device 400, in four sequential stages of use, in accordance with some embodiments.

The assembled state (FIG. 4A) is the same as the corresponding state shown in FIG. 3A.

The first motion differs from the deployment scheme of FIG. 3A-D, in that the first motion advances the pusher wire 114 distally, to deploy the first anchor 108, but does not advance the tube pusher 124 distally. In the state after the first motion (FIG. 4B), the tube pusher 124 is positioned at the same location as in the assembled state (FIG. 4A), which is proximal to where the tube pusher 124 is located in the example of FIG. 3B.

The second motion differs from the deployment scheme of FIG. 3A-D, in that the second motion retracts the pusher wire 114 farther than the assembled state (FIG. 4A), to position the teeth 116 inside the second anchor 112. In the state after the second motion (FIG. 4C), the teeth 116 are positioned proximal to the corresponding position in the assembled state (FIG. 4A).

The third motion advances the pusher wire 114 distally, but does not move the tube pusher 124. Note that in the configuration of FIGS. 4A-D, a push button 3 (FIG. 5) and a handle 5 (FIG. 5) can be configured such that a proximal or distal motion of the push button 3 on the handle 5 does not move the tube pusher 124 proximally or distally.

The anchor deployment schemes of FIGS. 2-4 are but three examples. Other suitable anchor deployment schemes can also be used. FIGS. 5-11 show an example of a full device that uses the first deployment scheme (FIGS. 2A-D). It will be understood that one of ordinary skill in the art can modify the elements of the full device to use the second deployment scheme (FIGS. 3A-D), the third deployment scheme (FIGS. 4A-D), or any other suitable deployment scheme.

FIG. 5A shows a perspective view of an example of the repair device 100 prior to use, in accordance with some embodiments. FIG. 5B shows a cutaway view of the distal portion of the repair device 100 of FIG. 5A, in accordance with some embodiments.

The device of FIGS. 5A and 5B can include the elements shown in FIG. 1, but with additional elements and a more realistic package design. Although many of the elements in FIGS. 5A and 5B are present in FIG. 1, it is instructive to discuss them in the context of the augmented device shown in FIGS. 5A and 5B.

The repair device 100 includes a needle 102 at its distal end. The needle 102 can be shaped as a cylindrical tube, with a tip sharp enough to pierce tissue. In some examples, the tip is angled. The needle 102 can define a bore therethrough. In some examples, the needle 102 and bore are shaped so that when a surgeon advances the needle 102 through tissue, the needle pierces the tissue without clogging the bore. The repair device 100 can store the anchors and anchor deployment mechanism in the bore of the needle 102.

A first anchor 108 can be positioned in the bore of the needle 102 and proximal to the tip of the needle 102. The first anchor 108 can be shaped as a cylinder, so that the first anchor 108 can slide over additional elements during assembly of the repair device 100, and so that a deployment mechanism can grip the first anchor 108 from an interior of the first anchor 108.

The deployment mechanism includes a pusher wire 114, and teeth 116 positioned on a distal end of the pusher wire 114. In some example, a distal portion of the pusher wire 114 can be laser-cut to impart additional flexibility to the pusher wire 114, so that the pusher wire 114 can more easily navigate a curved distal end of the needle 102. The teeth 116 are angled to catch and engage on the interior of the first anchor 108 when the pusher wire 114 and teeth 116 are advanced distally with respect to the first anchor 108, but slide along the interior of the first anchor 108 non-damagingly when the pusher wire 114 and teeth 116 are retracted proximally with respect to the first anchor 108. The repair device 100 can be assembled such that the first anchor 108 can be slid distally over the pusher wire 114 and teeth 116, or, equivalently, the pusher wire 114 and teeth 116 can be retracted proximally through the interior of the first anchor 108.

During use of the repair device 100, the surgeon pierces tissue with the needle 102, guides the needle 102 to a suitable location and orientation, then deploys the first anchor 108. To deploy the first anchor 108, the surgeon distally advances push button 3 with respect to a handle 5. The push button 3 is coupled to a distal end or a distal portion of a tube pusher assembly 6 (which includes the pusher wire 114 and teeth 116), and the distal motion of the push button 3 forces the tube pusher assembly 6 in a distal direction. The teeth 116 engage the interior of the first anchor 108, and push the first anchor 108 out of the bore of the needle 102 and distally past the distal end of the needle 102.

Figure 6A:
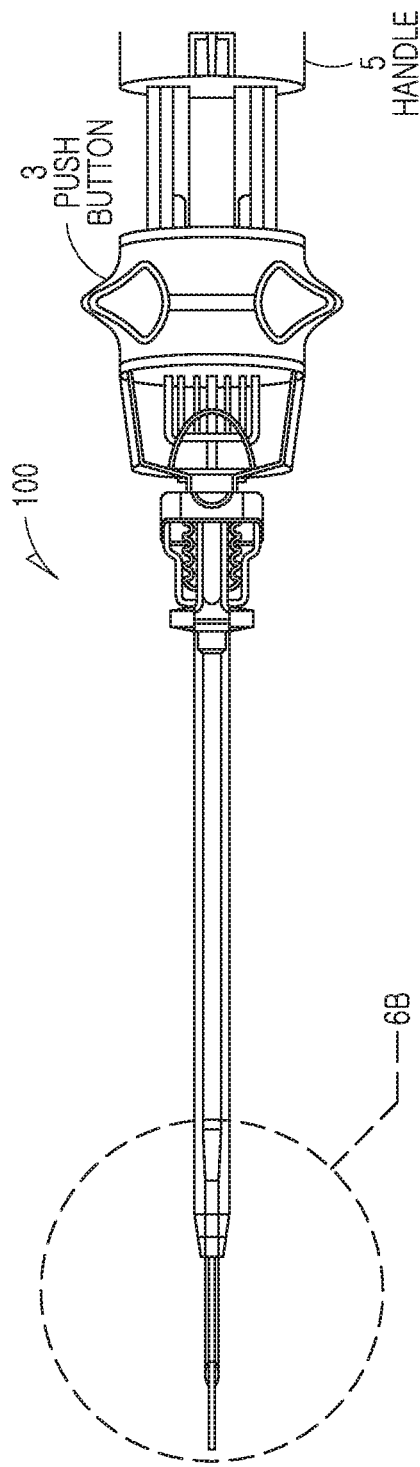
FIG. 6A shows a perspective view of the example of the repair device of FIG. 5A, after the first anchor has been deployed, in accordance with some embodiments.
Figure 6B:
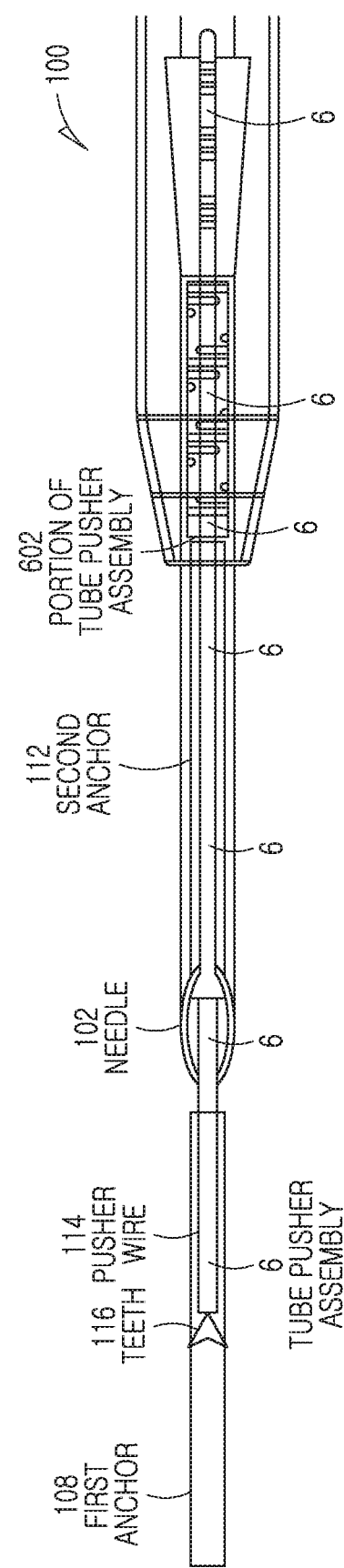
FIG. 6B shows a cutaway view of the distal portion of the repair device of FIG. 6A, in accordance with some embodiments.

FIG. 6A shows a perspective view of the example of the repair device 100 of FIG. 5A, after the first anchor has been deployed, in accordance with some embodiments. FIG. 6B shows a cutaway view of the distal portion of the repair device 100 of FIG. 6A, in accordance with some embodiments.

Compared with the views of FIGS. 5A and 5B, in FIGS. 6A and 6B, the push button 3 has been advanced distally, the tube pusher assembly 6 (including the pusher wire 114 and teeth 116) has been advanced distally, the first anchor has been forced distally out of the bore of the needle 102 and has been deployed at a suitable location in the bone or tissue, and the tube pusher assembly 6 has forced the second anchor 112 distally within the bore of the needle 102. In some examples, the tube pusher assembly 6 includes a portion 602 extending laterally beyond a diameter of the second anchor 112, so that when the tube pusher assembly 6 is forced distally, the portion 602 forces the second anchor 112 distally.

In some examples, the repair device 100 can emit an audible click when the push button 3 is fully advanced distally. The click is produced by at least one outward-biased tab on the tube pusher assembly 6 snapping into a corresponding inward-facing step on the handle 5 or on an element attached to the handle 5. By snapping into the step, the outward-biased tab also blocks the tube pusher assembly 6 from moving proximally beyond the location at which the snapping occurs, with respect to the handle 5, but still allows the tube pusher assembly 6 to move distally, with respect to the handle 5.

FIG. 7A shows a perspective view of the example of the repair device 100 of FIGS. 5-6, after the first anchor has been deployed, and after the push button 3 has been retracted proximally to its original location, in accordance with some embodiments. FIG. 7B shows a cutaway view of the distal portion of the repair device 100 of FIG. 7A, in accordance with some embodiments.

When the push button 3 is retracted proximally, the tube pusher assembly 6 is also retracted proximally while the second anchor 112 remains stationary. The proximal retraction places the teeth 116 within the interior of the second anchor 112, so that a subsequent distal movement of the pusher wire 114 and teeth 116 can engage the interior of the second anchor 112 and push the second anchor 112 out of the bore of the needle 102, thereby deploying the second anchor 112 at a suitable location in the bone or tissue.

FIG. 7A reveals several of the outward-biased tabs 702 on the tube pusher assembly 6, which snap into corresponding steps on a front end reversed curve sub assembly 7 (FIG. 11) that is attached to the handle 5. These tabs 702 emit the audible click that alerts the surgeon that the push button 3 is fully advanced distally (as in FIGS. 6A and 6B). These tabs 702, when snapped into the corresponding steps, are coupled to the second anchor 112 and therefore hold the second anchor 112 at the same location, with respect to the handle 5, when the push button 3 and tube pusher assembly 6 are retracted proximally (as in FIGS. 7A and 7B).

Figure 8A:
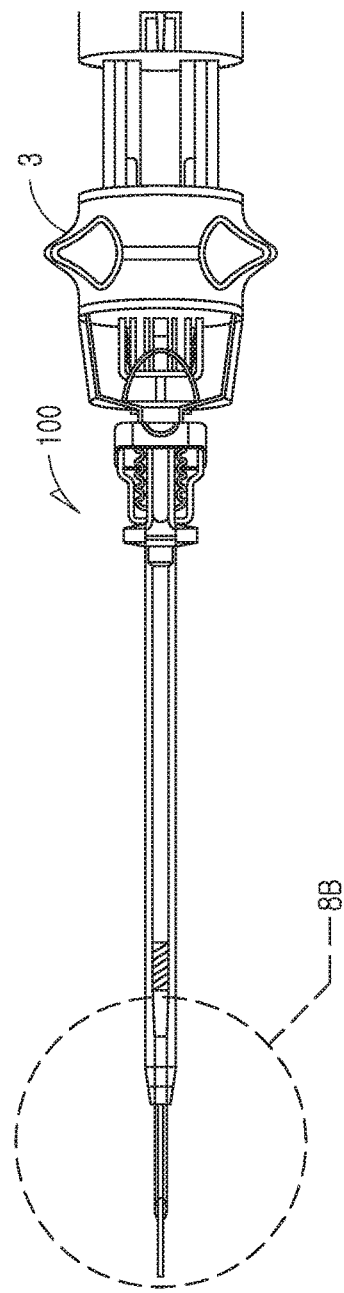
FIG. 8A shows a perspective view of the example of the repair device of FIGS. 5-7, as the second anchor is being deployed, in accordance with some embodiments.
Figure 8B:
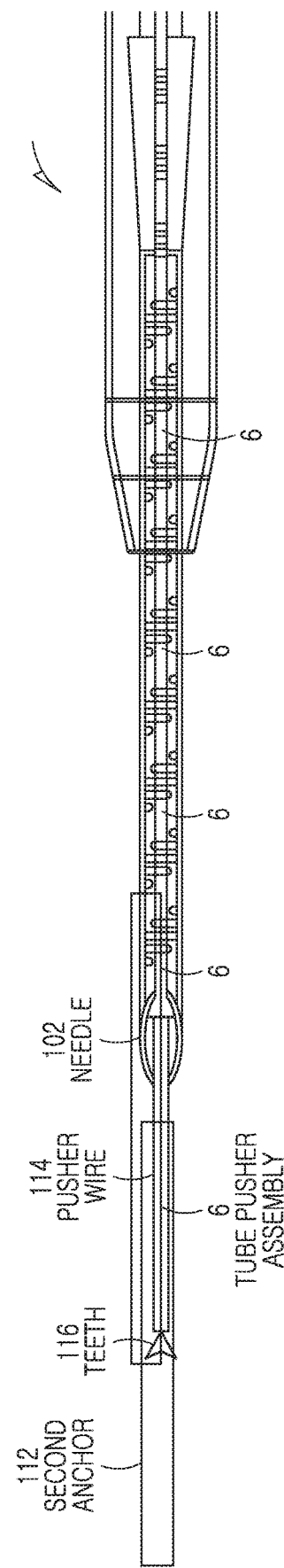
FIG. 8B shows a cutaway view of the distal portion of the repair device of FIG. 8A, in accordance with some embodiments.

FIG. 8A shows a perspective view of the example of the repair device 100 of FIGS. 5-7, as the second anchor is being deployed, in accordance with some embodiments. FIG. 8B shows a cutaway view of the distal portion of the repair device 100 of FIG. 8A, in accordance with some embodiments.

Compared with the views of FIGS. 7A and 7B, in FIGS. 8A and 8B, the push button 3 has been advanced distally a second time, the tube pusher assembly 6 (including the pusher wire 114 and teeth 116) has been advanced distally a second time, and the second anchor has been forced distally out of the bore of the needle 102 and has been deployed at a suitable location in the bone or tissue.

Figure 11:
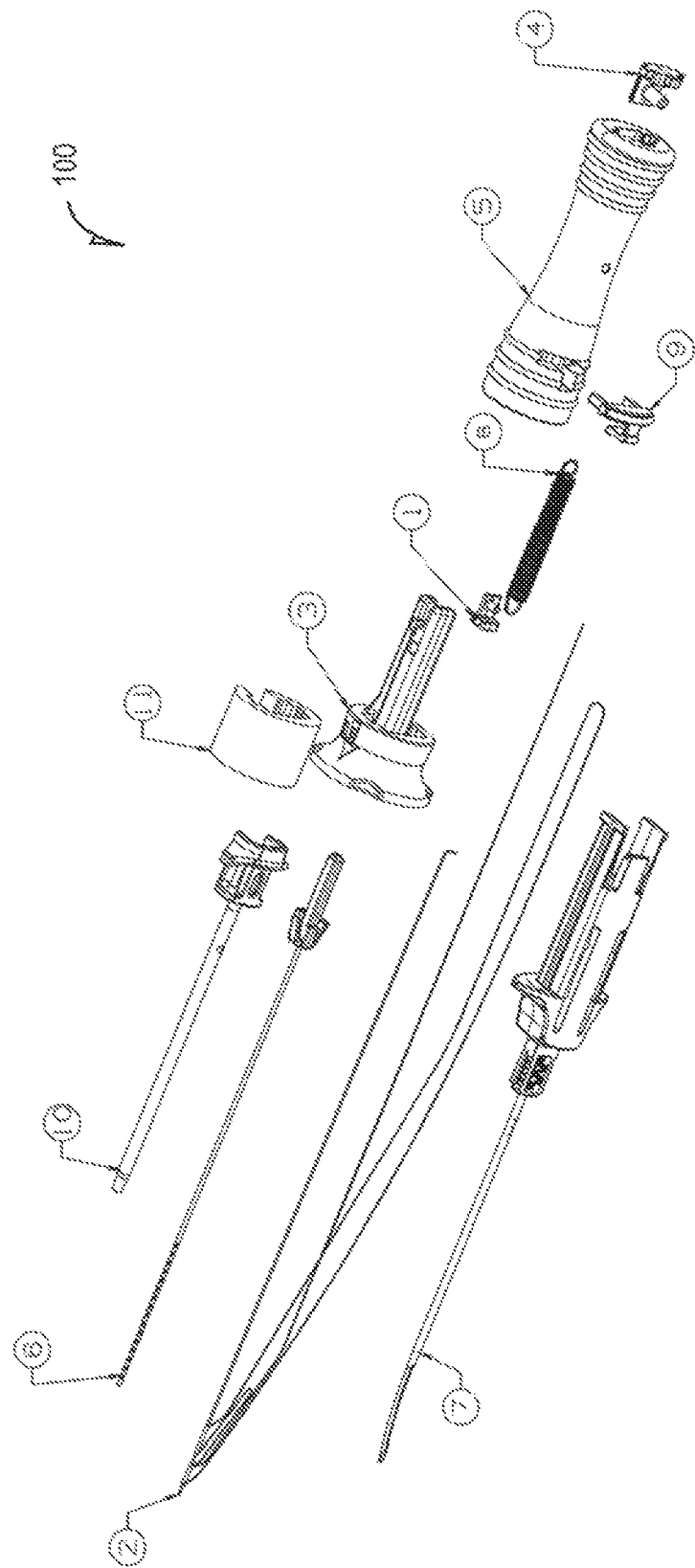
FIG. 11 shows an exploded view of the repair device of FIG. 9, in accordance with some embodiments.

In some examples, the repair device 100 can emit a second audible click when the push button 3 is fully advanced distally. The click is produced by the outward-biased tabs 702 snapping into another set of corresponding inward-facing steps on the handle 5 or on an element attached to the handle 5, such as the front end reversed curve sub assembly 7 (FIG. 11).

Once the second anchor is deployed, the surgeon can withdraw the repair device 100 proximally from the second anchor.

Figure 9:
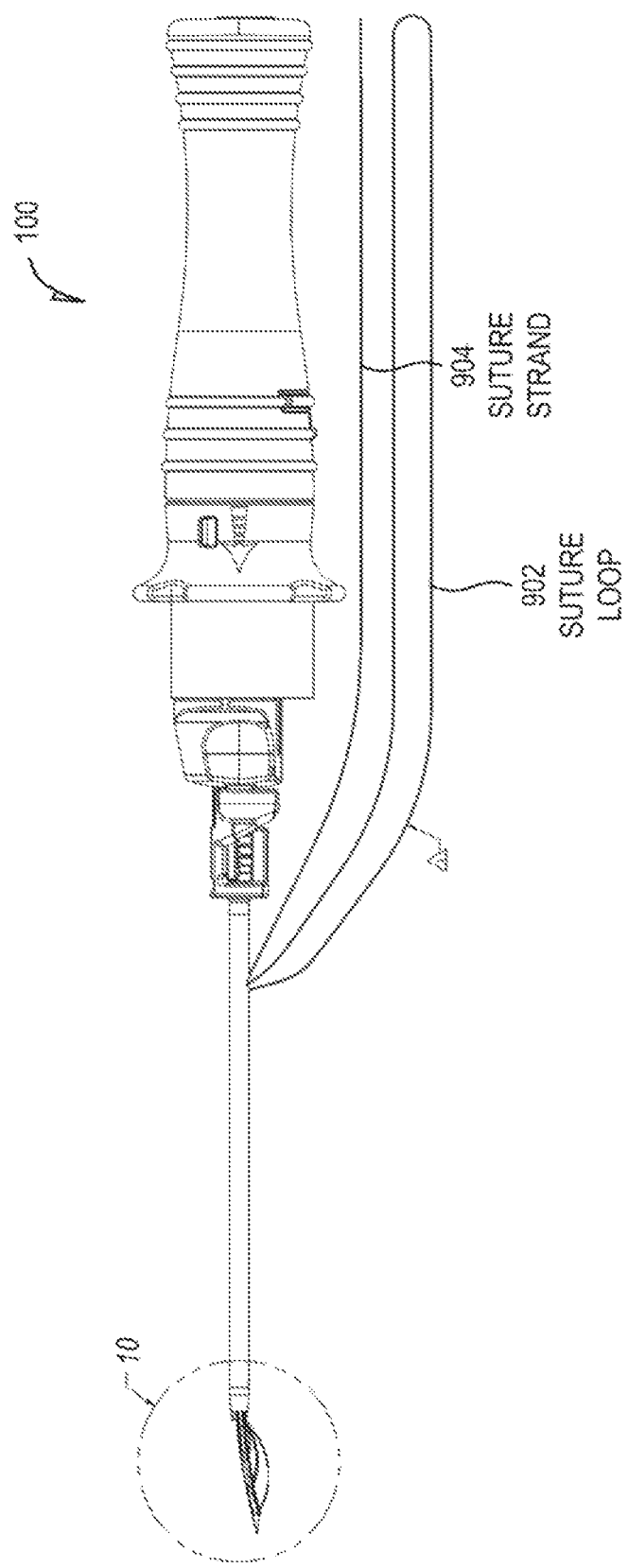
FIG. 9 shows a side view of an example of a repair device, including the suture loop and single strand of suture, in accordance with some embodiments.

FIG. 9 shows a side view of an example of a repair device 100, including the suture loop 902 and single strand 904 of suture, in accordance with some embodiments. During the advancing and retracting of the push button 3, as in FIGS. 5-8, the surgeon can take care to ensure that the suture loop 902 and suture strand 904 are not tangled and can be accessed after the anchors have been deployed.

Figure 10:
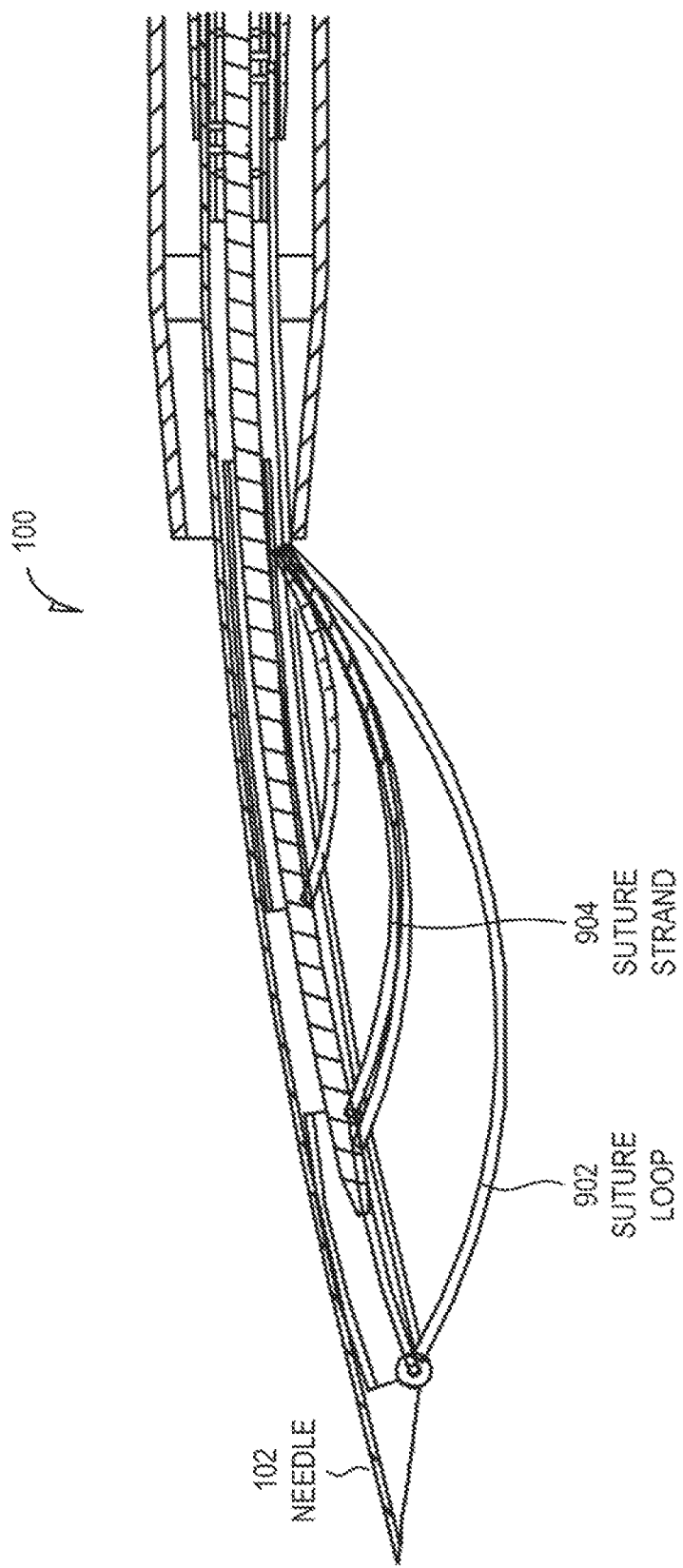
FIG. 10 shows a close-up side cross-sectional view of a distal end of the repair device of FIG. 9, including the suture loop and single strand of suture, in accordance with some embodiments.

FIG. 10 shows a close-up side cross-sectional view of a distal end of the repair device 100 of FIG. 9, including the suture loop 902 and single strand 904 of suture, in accordance with some embodiments.

FIG. 11 shows an exploded view of the repair device 100 of FIG. 9, in accordance with some embodiments. The configuration of elements in FIG. 11 is but one example; other suitable configurations can also be used.

During assembly of the repair device 100, first and second anchors (not shown) can be loaded onto a proximal end of a pusher wire subassembly 2, and advanced distally along the a pusher wire subassembly 2. The pusher wire subassembly 2, including the first and second anchors, can be loaded into a needle assembly 7 (also referred to as a front end reversed curve subassembly).

A tube pusher assembly 6 can be inserted proximally into a distal end of a push button 3. A distal end of the tube pusher assembly 6 can be inserted into a distal end of the needle assembly 7. The tube pusher assembly 6 can be fed proximally through a bore of the needle assembly 7 until the proximal end of the tube pusher assembly 6 is at or near a proximal end of the needle assembly 7.

A proximal end or proximal portion of the tube pusher assembly 6 can be locked to the push button 3 as follows. A wire lock 1 has a profile that matches a cut-out on the push button 3. The wire lock 1 can be inserted into the cut-out on the push button 3, thereby pinching a proximal end of a wire of the tube pusher. The wire can be bent by ninety degrees at the pinch point. An extra proximal portion of the wire, which can extend proximally beyond the pinch point, can be trimmed.

The wire lock can include a post that engages a distal end of a tension spring 8 (also referred to as an extension spring). A proximal end of the tension spring 8 can be fed proximally through an interior of a handle 5. The needle assembly 7 can include one or more outwardly-biased wings near its proximal end. These wings plug into the handle 5. A handle lock 9 (also referred to as a front end lock) can be inserted into a wall of the handle 5. Two prongs on the handle lock 9 can force the wings on the needle assembly 7 radially outward, and can prevent the needle assembly 7 from being detached from the handle 5.

A back 4 (also referred to as a spring retainer) can include a post that engages a proximal end of the handle 5, and, through the tension spring 8, can lock the push button 3 and tube pusher assembly 6 to the handle 5.

A piece of repair foam 11 can be packed with the repair device 100. The repair foam 11 can be positioned distal to the push button 3, and can prevent the push button 3 from moving distally prior to use of the repair device 100. A surgeon removes the repair foam 11 just prior to use of the repair device 100.

An adjustable depth stop assembly 10 can set a depth for the needle assembly 7, corresponding to how deep the tube pusher assembly 6 can extend distally beyond a distal end of the needle assembly 7, when the push button 3 is positioned at the proximal end of its range of travel, with respect to the handle 5. In some examples, the adjustable depth stop assembly 10 can include a window that blocks all but one labeled mark on the handle, so that as a surgeon adjusts the adjustable depth stop assembly 10, the surgeon can see a labeled mark corresponding to the selected depth. The series of labeled marks can include numerals corresponding to various depths.

In each of the configurations presented thus far, a pusher wire can extend through an interior of the anchors, and a tube pusher can extend over the pusher wire. In alternate configurations, the pusher wire can extend over the anchors (e.g., the pusher wire can have a hollow interior and can extend around an exterior of the anchors). Such a pusher wire can include teeth that extend inward and can engage an exterior of the anchors. For these alternate configurations, the tube pusher can be positioned inside the pusher wire and can engage a proximal end of the second anchor. In still other configurations, the proximal anchor can be positioned inside of a tube inside the needle, the tube can be advance to deploy the distal anchor, and a pusher inside the inner tube can be advanced to deploy the proximal anchor. In still other configurations, the pusher wire can route around an exterior of the anchors and engage the exterior of the anchors. For example, such a pusher wire can engage anchors shapes as a flat braid sleeve, rather than cylindrical.

Figure 12:
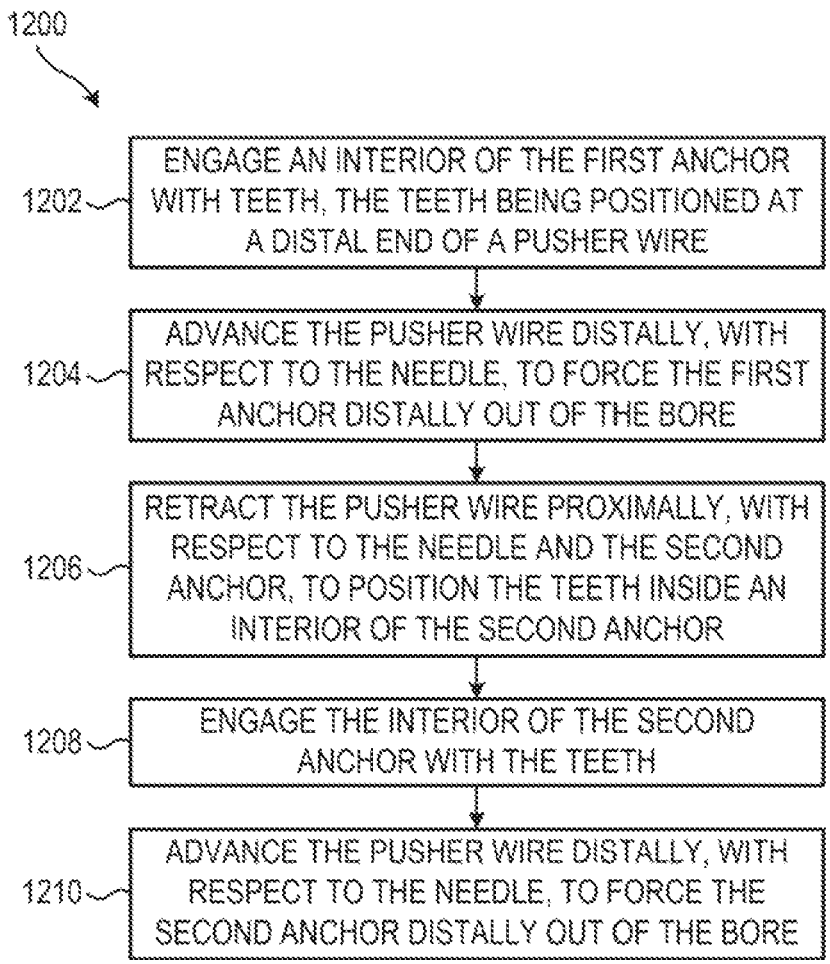
FIG. 12 shows a flow chart of an example of a method for deploying first and second anchors from a distal end of a bore of a needle, in accordance with some embodiments.

FIG. 12 shows a flow chart of an example of a method 1200 for deploying first and second anchors from a distal end of a bore of a needle, in accordance with some embodiments. The method 1200 can be executed by a repair device 100 (FIG. 1), or another suitable repair device. The method 1200 is but one example for deploying first and second anchors from a distal end of a bore of a needle; other suitable methods can also be used.

At operation 1202, the repair device can engage an interior of the first anchor with teeth. The teeth can be positioned at a distal end of a pusher wire.

At operation 1204, the repair device can advance the pusher wire distally, with respect to the needle, to force the first anchor distally out of the bore.

At operation 1206, the repair device can retract the pusher wire proximally, with respect to the needle and the second anchor, to position the teeth inside an interior of the second anchor.

At operation 1208, the repair device can engage the interior of the second anchor with the teeth.

At operation 1210, the repair device can advance the pusher wire distally, with respect to the needle, to force the second anchor distally out of the bore.

In some examples, the method 1200 can further include pushing the second anchor distally from a first position within the bore to a second position within the bore. In some examples, the second anchor can be pushed distally at the same time that the first anchor is forced distally out of the bore.

FIGS. 13-29 show views of various stages of a specific example of how a surgeon can use a meniscal repair device, such as 100 (FIG. 1). This is but one example of a surgical repair procedure; other suitable examples can also be used.

Figure 13:
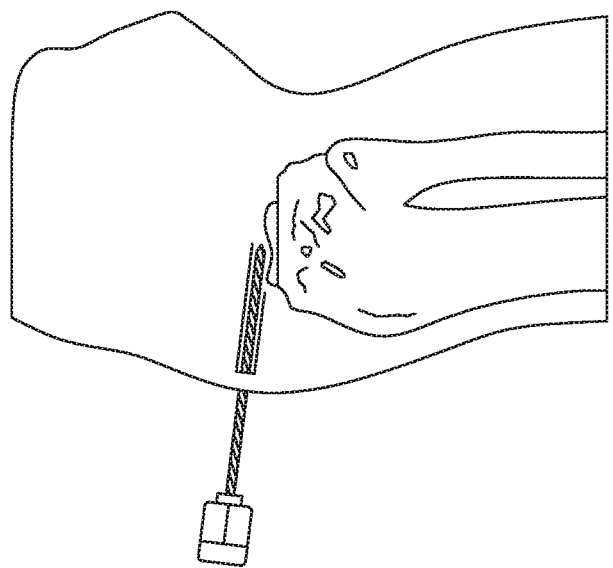

First, the surgeon can perform a diagnostic arthroscopy. During the diagnostic arthroscopy, the surgeon can assess a location of the meniscal tear and determine the reparability of the lesion. The surgeon can determine an optimum medial portal placement using an 18-gauge spinal needle and direct arthroscopic visualization to create a medial working portal. The surgeon can position the needle to enter just above the anterior medial meniscus parallel to the tibial joint surface (FIG. 13). The surgeon can avoid placing the portal too superior or inferior and can ensure that the medial portal is large enough to readily pass an inserter and a suture cutter. The surgeon can measure a distance from a back side of the meniscus to a desired needle penetration point at the repair site using a meniscal depth gauge.

Figure 14B:
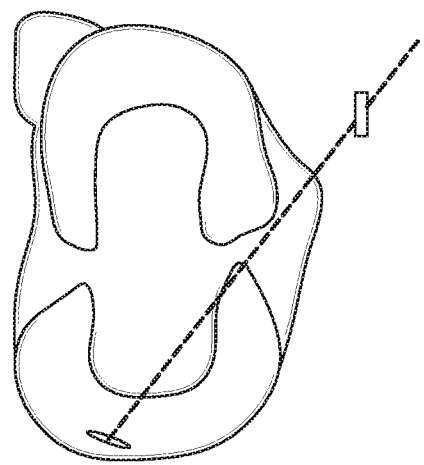
FIGS. 13-29 show views of various stages of a specific example of how a surgeon can use a meniscal repair device.
Figure 14A:
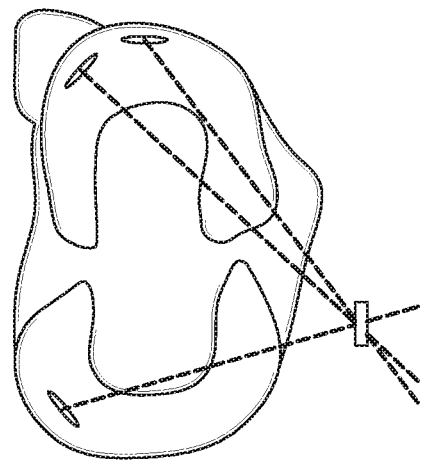
Figure 15:
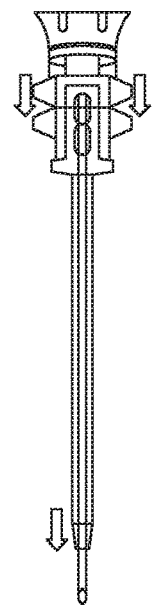

Next, the surgeon can decide on a suitable approach, choosing between a straight needle option and curved needle option and selecting a suitable portal. Meniscal repair devices are typically produced with one of two needle shapes, namely straight and curved. The surgeon can utilize a probe through the medial portal to help determine whether a straight or curved needle will position the implant optimally. Selecting between a straight or curved needle can depend on the location of the tear, and on the location of the portal (e.g., the location of the skin incision). It can be preferable to choose a needle shape so that the needle emerges through the back of the tissue and not the underside of the tissue. For most meniscal repairs, the surgeon can often select the curved needle option. The surgeon can approach posterior horn tears from the medial portal (FIG. 14A), including both medial and lateral tears. The surgeon can approach the mid-body tears from a contralateral portal (FIG. 14B). To adjust a needle depth, if needed, the surgeon can push down on a depth control slider in a forward motion to decrease the needle length exposed (FIG. 15).

Figure 17:
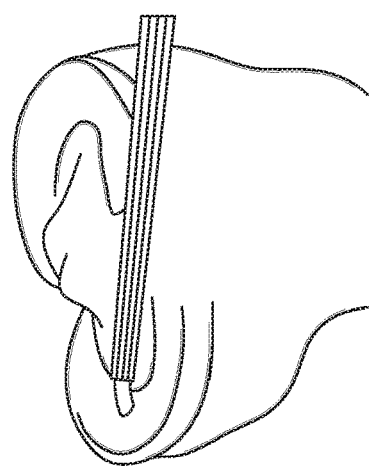
Figure 16:
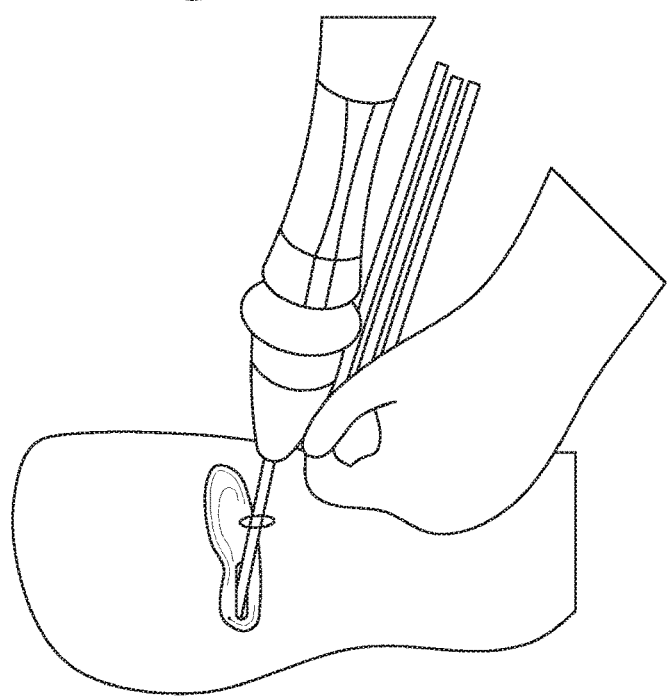
Figure 18:
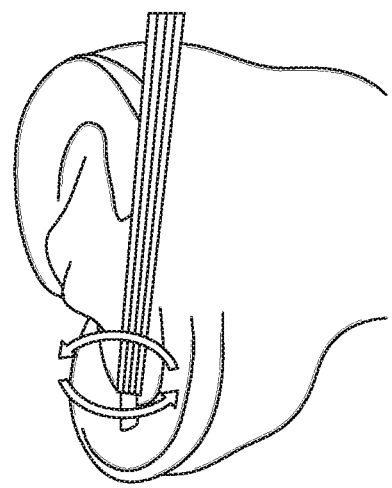

Next, the surgeon can position the meniscal repair device. The surgeon can advance the half pipe cannula sled through the selected portal to the meniscus. The surgeon can slide a sharp point against a half pipe cannula sled to advance the meniscal repair device into the joint. Advancing in this manner can limit catching the device on soft tissue. The surgeon can retract the half pipe cannula sled from the joint space once the meniscal repair device has been successfully inserted into the joint space (FIG. 16). Using the curved needle, the surgeon can enter the superior surface of the meniscus with the tip of the needle pointed inferiorly (FIG. 17). After the needle tip penetrates the meniscus, the surgeon can rotate the inserter 180 degrees (about a longitudinal axis of the meniscal repair device). The surgeon can then advance the needle just beyond the meniscocapsular junction (FIG. 18). This technique can help the meniscal implant pass completely through the meniscal tissue and the meniscocapsular junction.

Figure 19:
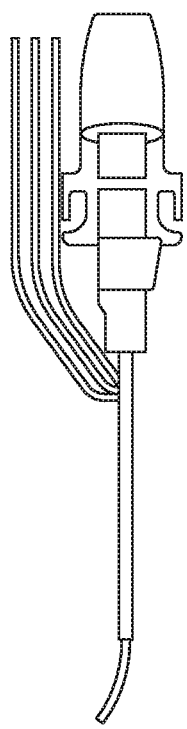
Figure 20C:
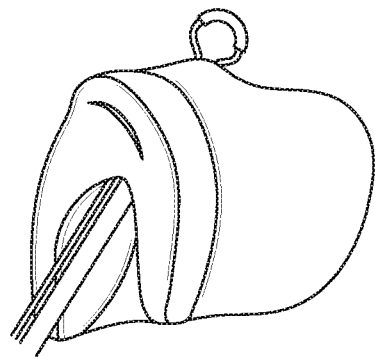
Figure 20B:
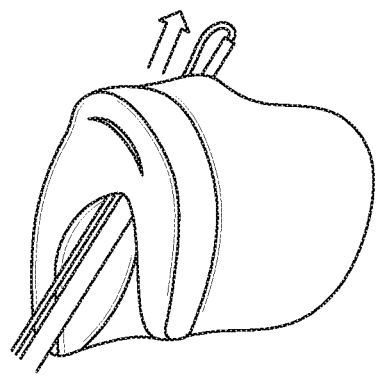
Figure 20A:
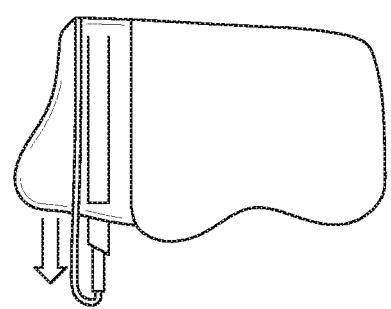
Figure 21:
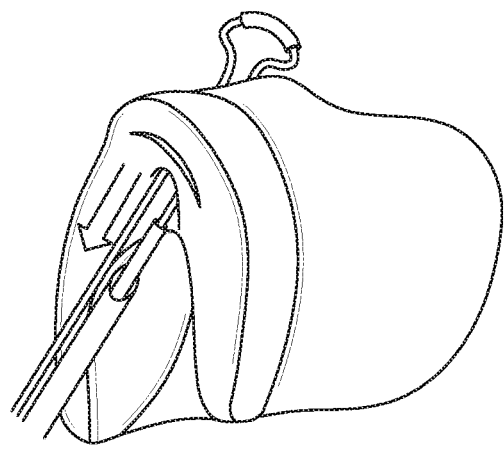

Next, the surgeon can deploy the first anchor. Once the meniscal repair device is inserted at the repair site, the surgeon can advance the push button forward to deploy the first anchor (e.g., push the first anchor out of the meniscal repair device) (FIG. 19). The meniscal repair device can emit an audible click to indicate that the implant has fully advanced through the meniscus (FIGS. 20A-C). The meniscal repair device can advance the second anchor forward, and place the needle in the location previously occupied by the first anchor. The surgeon can fully retract the push button and pull the needle tip gently out of the meniscus (FIG. 21).

Figure 23:
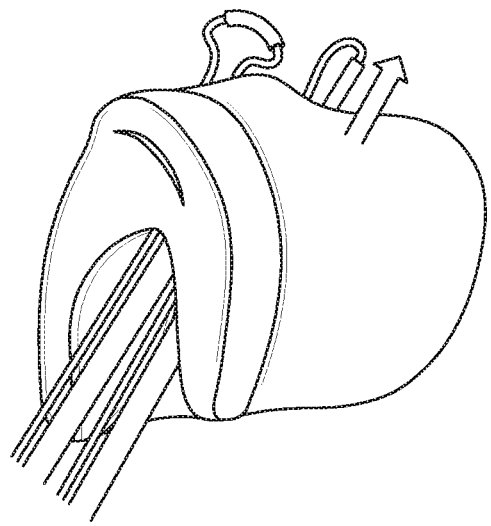
Figure 22:
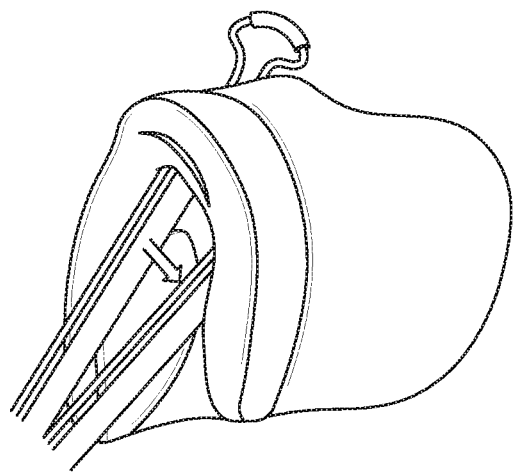
Figure 24:
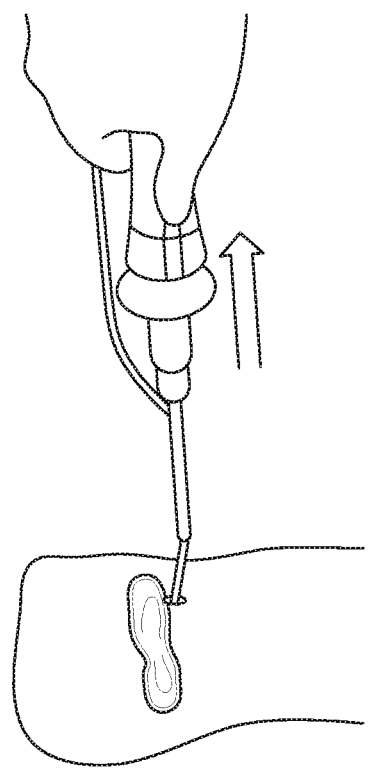

Next, the surgeon can deploy the second anchor. The surgeon can reposition the needle tip at a desired location and can advance the curved needle tip as described above (FIG. 22). The surgeon can advance the needle beyond the meniscocapsular junction. The surgeon can advance the push button forward to deploy the second anchor (e.g., push the second anchor out of the meniscal repair device) (FIG. 23). The surgeon can fully retract the push button and can completely remove the meniscal inserter from the joint (FIG. 24).

Figure 25:
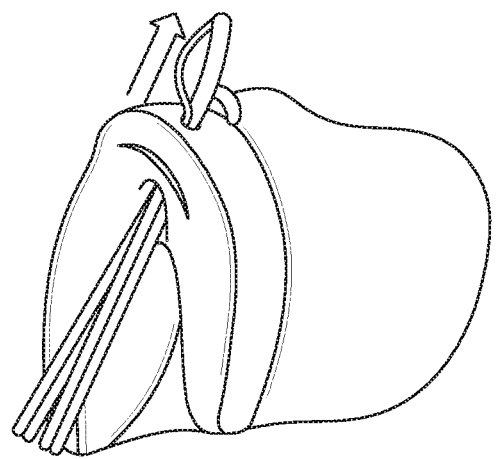
Figure 26:
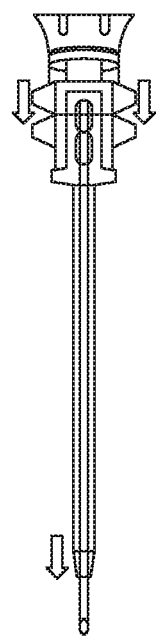

The surgeon can choose to position the anchors in a suitable pattern that is matched to the particular tear of the meniscus. In some examples, the surgeon can position one anchor above the other, in a so-called horizontal mattress pattern. In other examples, the surgeon can position the anchors side by side, in a so-called vertical mattress pattern. The vertical mattress stitching pattern can be well-suited for meniscal repairs due to its ability to achieve deep and superficial wound closure, edge eversion and precise vertical alignment of the superficial wound margins. The surgeon can insert the first anchor on the inferior meniscal rim. The surgeon can insert the second anchor superior to the tear on the meniscal rim. Implants in this superior meniscal location can require shorter distances of deployment, since the depth of meniscus can be less than the depth at the inferior location (FIG. 25). To decrease the needle depth for the superior position, the surgeon can adjust an adjustable depth stop until the needle reaches a desired depth (FIG. 26).

Figure 27B:
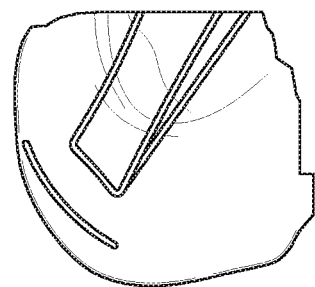
Figure 27A:
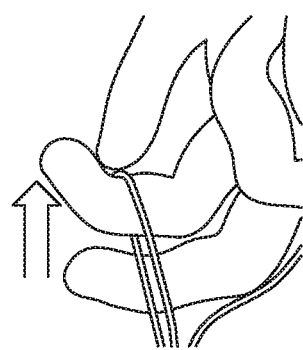
Figure 28:
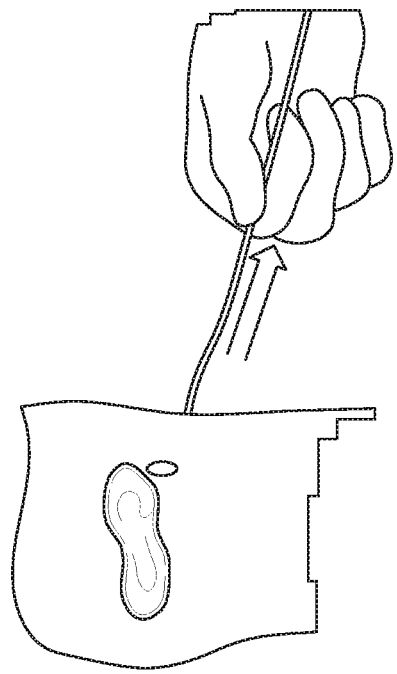

Next, the surgeon can tension the suture. After the surgeon retracts the meniscal repair device from the joint, a suture loop and a single strand can protrude from the portal. The suture loop and single strand can be formed from a single piece of suture run through itself, and configured as an adjustable loop. If the surgeon pulls on the loop, the loop does not increase in size. If the surgeon pulls on the single strand, the loop shrinks. Deploying the anchors as described above can produce a small loop of suture inside the joint, a larger loop of suture emerging from the skin, and a free strand emerging from the skin. The surgeon can use index and middle fingers to pull on the larger loop (in some cases, a blue/white side of the loop) with multiple short tugs to set the anchors at the repair site (FIG. 27A). The surgeon can pull on one side the larger loop until the surgeon is satisfied with the tension on the smaller loop. Advantageously, the suture loop can include segments having different colors or different patterns, which, when the anchors are deployed, can visually indicate which side of the loop the surgeon should pull to set the loop tension. In a specific example, the segment to be pulled includes a blue suture with a white tracer, while the segment that should not be pulled is all white. In some examples, when the blue/white portion of the suture loop no longer moves in response to the tugs, the anchor is fully set. The surgeon can visually confirm, with a scope, that the anchor is fully set at the repair site (FIG. 27B). The surgeon can pull the single strand (in some cases, colored white) to contract the large loop down to the surface of the meniscus. The surgeon can pull on the strand until tension on the second loop matches the tension of the first loop (FIG. 28). If desired, the surgeon can use a probe to check the repair site for appropriate tension.

Figure 29:
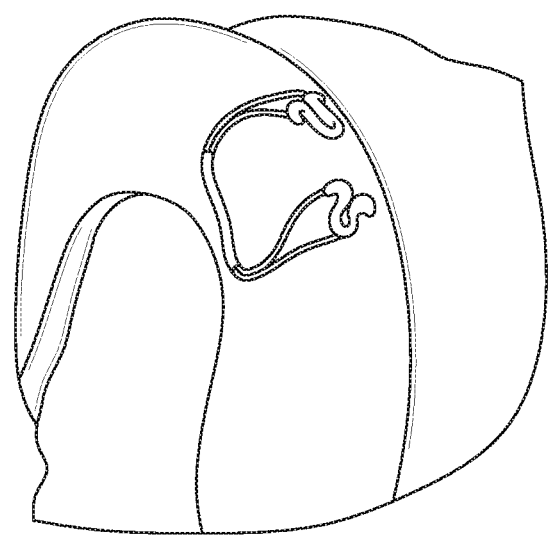

Finally, the surgeon can cut the suture. The surgeon can insert a cutter into the portal and advance the cutter to sever the suture, thereby completing fixation and repair of the meniscus (FIG. 29).

The meniscal repair device discussed in detail above improves over comparable meniscal repair devices. For example, the present meniscal repair device uses an anchor formed from a suture sleeve, which is preferable to using a hard plastic anchor, made from a relatively hard material, such as polyether ether ketone (PEEK). In cases where the suture pulls through the meniscal tissue, the anchor could be dislodged within the knee joint space. A hard plastic anchor could cause joint damage by moving within the joint space. The all-suture anchor of the present meniscal repair device would not cause such damage. As another advantage, the present meniscal repair device uses two suture strands across the tissue, rather than a single suture strand, which can distribute the suture force over a larger tissue area and therefore reduce the likelihood that suture will rip through the tissue. As still another advantage, the present can deploy the anchors without using any pre-tied suture knots, which in some cases could rub against the femur and potentially damage the femur.

To further illustrate the device and related method disclosed herein, a non-limiting list of examples is provided below. Each of the following non-limiting examples can stand on its own, or can be combined in any permutation or combination with any one or more of the other examples.

In Example 1, a repair device comprises: a needle defining a bore extending through a distal end of the needle; a cylindrical first anchor sized and shaped to be disposed in the bore proximal to a distal end of the bore; a cylindrical second anchor sized and shaped to be disposed in the bore proximal to the first anchor; and a pusher wire including teeth positioned at a distal end of the pusher wire, the teeth configured to: engage an interior of the first anchor; advance distally, with respect to the needle, to force the first anchor distally out of the bore; retract proximally, with respect to the needle and the second anchor, to position the teeth inside an interior of the second anchor; engage the interior of the second anchor; and advance distally, with respect to the needle, to force the second anchor distally out of the bore.

In Example 2, the device of Example 1 can optionally be configured such that the teeth are sized and shaped to: catch and engage on the interiors of the first and second anchors when the pusher wire and teeth are advanced distally with respect to the first and second anchors, respectively; and slide along the interiors of the first and second anchors non-damagingly when the pusher wire and teeth are retracted proximally with respect to the first and second anchors, respectively.

In Example 3, the device of any one or a combination of Examples 1-2 can optionally be configured such that the pusher wire has an outer diameter smaller than respective inner diameters of the first and second anchors, so that the pusher wire is non-engagingly slidable through the first and second anchors in the proximal and distal directions.

In Example 4, the device of any one or a combination of Examples 1-3 can optionally be configured to further comprise a tube pusher positioned over the pusher wire within the bore of the needle, the tube pusher having a distal portion that extends radially beyond an outer circumference of the second anchor, so that the tube pusher pushes the second anchor distally as the tube pusher advances distally within the bore of the needle.

In Example 5, the device of any one or a combination of Examples 1-4 can optionally be configured to further comprise a handle fixedly coupled to a proximal end of the needle; and a push button disposed on an exterior of the handle, the push button being slidable proximally and distally with respect to the handle between a first proximal position and a first distal position, the push button being coupled to the pusher wire so that proximal and distal movement of the push button produces proximal and distal movement of the pusher wire and teeth.

In Example 6, the device of any one or a combination of Examples 1-5 can optionally be configured such that the push button is slidable to the first distal position on the handle; and further comprising an adjustable depth stop assembly configured so that movement of the push button to the first distal position distally advances the teeth to a selectable distance beyond a distal end of the needle.

In Example 7, the device of any one or a combination of Examples 1-6 can optionally be configured such that the handle is configured to emit an audible click when the push button reaches the first distal position on the handle.

In Example 8, the device of any one or a combination of Examples 1-7 can optionally be configured such that the push button is slidable to a first proximal position on the handle; and the teeth are positioned within the first or second anchors when the push button is positioned at the first proximal position.

In Example 9, the device of any one or a combination of Examples 1-8 can optionally be configured such that the handle is configured to emit an audible click when the push button reaches the first proximal position on the handle.

In Example 10, the device of any one or a combination of Examples 1-9 can optionally be configured such that proximal motion of the push button does not move the tube pusher proximally.

In Example 11, the device of any one or a combination of Examples 1-10 can optionally be configured such that distal motion of the push button advances the tube pusher distally.

In Example 12, the device of any one or a combination of Examples 1-11 can optionally be configured such that the teeth are positioned within the first anchor when the push button is positioned at the first proximal position; the push button is slidable to a second proximal position on the handle; and the teeth are positioned within the second anchor when the push button is positioned at the second proximal position.

In Example 13, the device of any one or a combination of Examples 1-12 can optionally be configured such that the handle is configured to emit an audible click when the push button reaches the second proximal position on the handle.

In Example 14, the device of any one or a combination of Examples 1-13 can optionally be configured such that proximal or distal motion of the push button does not move the tube pusher proximally or distally.

In Example 15, the device of any one or a combination of Examples 1-14 can optionally be configured such that the first and second anchors are connected by an adjustable suture loop.

In Example 16, a method for deploying first and second anchors from a distal end of a bore of a needle can comprise: engaging an interior of the first anchor with teeth, the teeth being positioned at a distal end of a pusher wire; advancing the pusher wire distally, with respect to the needle, to force the first anchor distally out of the bore; retracting the pusher wire proximally, with respect to the needle and the second anchor, to position the teeth inside an interior of the second anchor; engaging the interior of the second anchor with the teeth; and advancing the pusher wire distally, with respect to the needle, to force the second anchor distally out of the bore.

In Example 17, the method of Example 16 can optionally further comprise: pushing the second anchor distally from a first position within the bore to a second position within the bore.

In Example 18, the method of any one or a combination of Examples 16-17 can optionally be configured such that the second anchor is pushed distally at the same time that the first anchor is forced distally out of the bore.

In Example 19, a repair device can comprise: a needle defining a bore extending through a distal end of the needle; a cylindrical first anchor disposed in the bore proximal to a distal end of the bore; a cylindrical second anchor disposed in the bore proximal to the first anchor and connected to the cylindrical first anchor by an adjustable suture loop; a pusher wire having an outer diameter smaller than respective inner diameters of the first and second anchors, so that the pusher wire is non-engagingly slidable through the first and second anchors in the proximal and distal directions, the pusher wire including teeth positioned at a distal end of the pusher wire, the teeth being sized and shaped to: catch and engage on interiors of the first and second anchors when the pusher wire and teeth are advanced distally with respect to the first and second anchors, respectively; and slide along the interiors of the first and second anchors non-damagingly when the pusher wire and teeth are retracted proximally with respect to the first and second anchors, respectively; a tube pusher positioned over the pusher wire within the bore of the needle, the tube pusher having a distal portion that extends radially beyond an outer circumference of the second anchor, so that the tube pusher pushes the second anchor distally as the tube pusher advances distally within the bore of the needle; a handle fixedly coupled to a proximal end of the needle; and a push button disposed on an exterior of the handle, the push button being slidable proximally and distally with respect to the handle between a first proximal position and a first distal position, the push button being coupled to the pusher wire so that proximal and distal movement of the push button produces proximal and distal movement of the pusher wire and teeth.

In Example 20, the device of Example 19 can optionally be configured such that the push button is slidable to the first distal position on the handle; wherein the handle is configured to emit an audible click when the push button reaches the first distal position on the handle; and further comprising an adjustable depth stop assembly configured so that movement of the push button to the first distal position distally advances the teeth to a selectable distance beyond a distal end of the needle.

While this invention has been described as having example designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A repair device, comprising:
   a needle defining a bore extending through a distal end of the needle;
   a deformable cylindrical first anchor sized and shaped to be disposed in the bore proximal to a distal end of the bore;
   a deformable cylindrical second anchor sized and shaped to be disposed in the bore proximal to the first anchor; and
   a pusher wire including teeth positioned at a distal end of the pusher wire, the teeth configured to:
   be positioned entirely within an interior of the deformable cylindrical first anchor;
   be advanced distally with respect to the needle while remaining entirely within the interior of the deformable cylindrical first anchor to force the deformable cylindrical first anchor distally out of the bore through engagement of the teeth with the interior of the deformable cylindrical first anchor;
   be retracted proximally, with respect to the needle and the deformable cylindrical second anchor, to position the teeth entirely within an interior of the deformable cylindrical second anchor; and
   be advanced distally with respect to the needle while remaining entirely within the interior of the deformable cylindrical second anchor to force the deformable cylindrical second anchor distally out of the bore through engagement of the teeth with the interior of the deformable cylindrical second anchor.

2. The repair device of claim 1, wherein the teeth are sized and shaped to:
   catch on the interiors of the deformable cylindrical first and second anchors when the pusher wire and teeth are advanced distally with respect to the deformable cylindrical first and second anchors, respectively; and
   slide along the interiors of the deformable cylindrical first and second anchors when the pusher wire and teeth are retracted proximally with respect to the deformable cylindrical first and second anchors, respectively.

3. The repair device of claim 1, wherein the pusher wire has an outer diameter smaller than the inner diameters of the deformable cylindrical first and second anchors, so that the pusher wire is slidable through the deformable cylindrical first and second anchors in the proximal and distal directions.

4. The repair device of claim 1 further comprising a tube pusher positioned over the pusher wire within the bore of the needle, the tube pusher having a distal portion that extends radially beyond an outer circumference of the second anchor, so that the tube pusher pushes the second anchor distally as the tube pusher advances distally within the bore of the needle.

5. The repair device of claim 1 further comprising:
   a handle fixedly coupled to a proximal end of the needle, and
   a push button disposed on an exterior of the handle, the push button being slidable proximally and distally with respect to the handle between a first proximal position and a first distal position, the push button being coupled to the pusher wire so that proximal and distal movement of the push button produces proximal and distal movement of the pusher wire and teeth.

6. The repair device of claim 5, further comprising an adjustable depth stop assembly configured so that movement of the push button to the first distal position distally advances the teeth to a selectable distance beyond a distal end of the needle.

7. The repair device of claim 6, wherein the handle is configured to emit an audible click when the push button reaches the first distal position on the handle.

8. The repair device of claim 5, wherein the teeth are positioned within the deformable cylindrical first or second anchors when the push button is positioned at the first proximal position.

9. The repair device of claim 8, wherein the handle is configured to emit an audible click when the push button reaches the first proximal position on the handle.

10. The repair device of claim 8 further comprising a tube pusher positioned over the pusher wire within the bore of the needle, the tube pusher having a distal portion that extends radially beyond an outer circumference of the second anchor, so that the tube pusher pushes the second anchor distally as the tube pusher advances distally within the bore of the needle, wherein proximal motion of the push button does not move the tube pusher proximally.

11. The repair device of claim 10, wherein distal motion of the push button advances the tube pusher distally.

12. The repair device of claim 8, wherein:
    the teeth are positioned within the deformable cylindrical first anchor when the push button is positioned at the first proximal position; and
    the teeth are positioned within the deformable cylindrical second anchor when the push button is positioned at the second proximal position.

13. The repair device of claim 12, wherein the handle is configured to emit an audible click when the push button reaches the second proximal position on the handle.

14. The repair device of claim 12 further comprising a tube pusher positioned over the pusher wire within the bore of the needle, the tube pusher having a distal portion that extends radially beyond an outer circumference of the second anchor, so that the tube pusher pushes the second anchor distally as the tube pusher advances distally within the bore of the needle, wherein proximal or distal motion of the push button does not move the tube pusher proximally or distally.

15. The repair device of claim 1, wherein the deformable cylindrical first and second anchors are connected by an adjustable suture loop.

16. A repair device, comprising:
    a needle defining a bore extending through a distal end of the needle;
    a deformable cylindrical first anchor disposed in the bore proximal to a distal end of the bore;
    a deformable cylindrical second anchor disposed in the bore proximal to the deformable cylindrical first anchor and connected to the deformable cylindrical first anchor by an adjustable suture loop;

a pusher wire having an outer diameter smaller than respective inner diameters of the deformable cylindrical first and second anchors, so that the pusher wire is slidable through the deformable cylindrical first and second anchors in the proximal and distal directions, the pusher wire including teeth positioned at a distal end of the pusher wire, the teeth being sized and shaped to: (i) be positioned entirely within and catch on interiors of the deformable cylindrical first and second anchors when the pusher wire and teeth are advanced distally to distally advance the deformable cylindrical first and second anchors, respectively, and ii) be slid slide along the interiors of the deformable cylindrical first and second anchors when the pusher wire and teeth are retracted proximally with respect to the deformable cylindrical first and second anchors, respectively;

a tube pusher positioned over the pusher wire within the bore of the needle, the tube pusher having a distal portion that extends radially beyond an outer circumference of the deformable cylindrical second anchor, so that the tube pusher pushes the deformable cylindrical second anchor distally as the tube pusher advances distally within the bore of the needle;

a handle fixedly coupled to a proximal end of the needle; and a push button disposed on an exterior of the handle, the push button being slidable proximally and distally with respect to the handle between a first proximal position and a first distal position, the push button being coupled to the pusher wire so that proximal and distal movement of the push button produces proximal and distal movement of the pusher wire and teeth.

17. The repair device of claim 16, wherein the handle is configured to emit an audible click when the push button reaches the first distal position on the handle; and further comprising an adjustable depth stop assembly configured so that movement of the push button to the first distal position distally advances the teeth to a selectable distance beyond a distal end of the needle.

* * * * *